United States Patent [19]

McAndrew et al.

[11] Patent Number: 5,517,405
[45] Date of Patent: May 14, 1996

[54] EXPERT SYSTEM FOR PROVIDING INTERACTIVE ASSISTANCE IN SOLVING PROBLEMS SUCH AS HEALTH CARE MANAGEMENT

[75] Inventors: Peter D. McAndrew, Centerbrook; David L. Potash, Glastonbury; Brian Higgins, East Haven; Jeff Wayand, Granby; Joe Held, West Hartford, all of Conn.

[73] Assignee: Aetna Life and Casualty Company, Hartford, Conn.

[21] Appl. No.: 136,649

[22] Filed: Oct. 14, 1993

[51] Int. Cl.⁶ .......................... G06F 159/00; G06F 17/60
[52] U.S. Cl. .............................. 364/401; 395/924
[58] Field of Search .................... 364/413.01, 413.02, 364/419.19, 402, 406, 401; 395/12, 51, 911, 924, 925, 934

[56] References Cited

U.S. PATENT DOCUMENTS

| | | | |
|---|---|---|---|
| 4,491,725 | 1/1985 | Pritchard | 364/406 |
| 4,839,822 | 6/1989 | Dormond et al. | 364/413.02 |
| 4,945,476 | 7/1990 | Bodick et al. | 364/413.02 |
| 4,975,840 | 12/1990 | DeTore et al. | |
| 4,987,538 | 1/1991 | Johnson et al. | 364/413.01 |
| 5,006,998 | 4/1991 | Yasunobu et al. | |
| 5,043,891 | 8/1991 | Goldstein et al. | |
| 5,148,366 | 9/1992 | Buchanan et al. | |
| 5,191,522 | 3/1993 | Bosco et al. | |
| 5,239,617 | 8/1993 | Gardner et al. | 395/12 |
| 5,253,164 | 10/1993 | Holloway et al. | |
| 5,265,010 | 11/1993 | Evans-Paganelli et al. | 364/413.02 |
| 5,274,749 | 12/1993 | Evans | 395/51 |
| 5,297,042 | 3/1994 | Morita | 364/419.19 |
| 5,325,465 | 6/1994 | Hung et al. | 364/419.19 |
| 5,333,237 | 7/1994 | Stefanopoulos et al. | 395/934 |

OTHER PUBLICATIONS

E. Shortliffe, "Computer Programs to Support Clinical Decision Making", JAMA Jul. 3, 1987 vol. 258, No. 1 pp. 61–66.
B. Silverman, "Building a Better Critic", IEEE Expert, Apr. 1992 pp. 18–25.
S. Mittal et al., "Patrec: A Knowledge–Directed Database for a Dagnostic Expert System", IEEE Computer, Sep. 1984 pp. 51–58.

*Primary Examiner*—Robert A. Weinhardt
*Attorney, Agent, or Firm*—Barry R. Lipsitz

[57] ABSTRACT

A problem solving expert system is provided which is particularly useful in managing the health care of individual patients. A description of a problem (e.g., medical condition) and a proposed solution therefor (e.g., medical procedure) is entered via a user interface. A topical library is searched to identify information relevant to the problem and proposed solution. Access to the identified information is available in either a full text or synopsis format, to assist a user in assessing the appropriateness of the proposed solution. An inference engine provides a recommendation to the user as to the appropriateness of the proposed solution based on information entered via the user interface and rules associated with the inference engine. A user can interact with the inference engine in either a structured or guided mode. The structured mode is directed to inexperienced users and dynamically generates questions in response to previous answers provided by the user to enable the inference engine to make its recommendation. The guided mode is directed to experienced users and provides a predefined questionnaire enabling the user to decide which questions to answer in order to obtain a recommendation.

21 Claims, 2 Drawing Sheets

EXPERT SYSTEM FOR PROVIDING INTERACTIVE ASSISTANCE IN SOLVING PROBLEMS SUCH AS HEALTH CARE MANAGEMENT

BACKGROUND OF THE INVENTION

The efficient management of health care has become both an economic and political issue. From time to time, a procedure recommended by a physician may not be the most prudent course to follow for a particular patient. Recently, health care insurers are becoming more involved in the decision as to what course of treatment to pursue for a particular medical condition. Such comprehensive case management can result in a more successful outcome for the patient at a lower cost.

In the past, the management of individual patient treatments has been provided on a transactional basis. In other words, each time a patient was diagnosed with a problem, a determination was made as to a recommended course of treatment for that diagnosis. After the treatment was undertaken, any further diagnoses and/or treatments were reviewed individually by the patient's insurer, without a comprehensive review of past diagnoses and treatments for the particular patient. Such a transactional review process can result in a patient undergoing a variety of treatments for the same condition, where an alternative treatment in the first place may have resulted in a better outcome for the patient at a lower cost for the insurer.

In order to provide a better level of health care management, the present invention provides a computer "expert system" for interactively assisting a user in solving problems, such as whether or not to certify a particular medical treatment for a diagnosed medical condition. The invention can be implemented using a relational database and graphical user interface for data capture and reporting. Dynamic decision support (e.g., as to whether or not to certify a medical procedure) provides information and recommendations to case managers, tailored to the experience level of the case manager, the level of the case manager's authority, and the relevant clinical situation. Policy and clinical guidelines can be authored centrally, distributed electronically and used locally by the case managers to ensure consistency in policy and decision making.

Significant productivity improvements and operational cost savings are provided by the invention. As reviewers (e.g., case managers) move through the workflow, they are supported by the system with information and guidelines tailored to their needs at that time. The information and guidelines are provided on a context-sensitive basis, based on a full awareness of the current medical situation.

Expert systems, per se, are well known. An example can be found in U.S. Pat. No. 4,648,044 issued on Mar. 3, 1987 for "Basic Expert System Tool." The '044 patent discloses a tool for building a knowledge system and running a consultation on a computer. As noted in the patent, knowledge systems are computer systems that emulate reasoning tasks by using an "inference engine" to interpret encoded knowledge of human experts stored in a "knowledge base." If the domain of the knowledge base, or scope of the problem is sufficiently narrow and a sufficiently large body of information is properly coded in the knowledge base, then performance that matches or exceeds the ability of a human expert can be achieved. In such a case, the knowledge system becomes an "expert system." The '044 patent is concerned with the building of an expert system, and not the implementation of such a system for a specific end use.

It would be advantageous to provide an expert system that interactively assists a user in solving problems such as the certification of a particular medical procedure for a given diagnosis. It would be further advantageous to provide such a system that provides a user with all of the information necessary to solve the problem. For example, in the medical context such information would include definitions of medical conditions and treatments, detailed articles from medical journals relating to the diagnosis and treatment, policy and clinical guidelines for use in assessing whether a proposed treatment is appropriate for the given diagnosis, and other relevant information such as basic definitions of the diagnosis and treatment.

It would be further advantageous to enable a user to selectively obtain full detailed information or a quick synopsis of the relevant information. This feature would allow more experienced users to quickly arrive at a decision without having to plod through a large amount of information that the user may already have knowledge of.

It would be still further advantageous to provide such an expert system that can be used by both experienced and inexperienced users. In order to enable inexperienced users to properly solve a problem, a highly structured approach should be provided to ensure that the user inputs all of the information necessary for the system to make a recommendation. An experienced user, on the other hand, should be able to properly solve problems with only minimal guidance from the system.

The present invention provides an expert problem solving computer system having the aforementioned advantages and useful for many different applications.

SUMMARY OF THE INVENTION

The invention provides a computer-based decision support tool for enabling users to decide whether to accept or reject a proposed solution to a problem. For example, in the health care field the decision tool can be used to recommend whether or not to accept a proposed treatment for a given medical condition. Four decision making models are provided for fostering appropriate decision making by users. In a specific embodiment, the decision making process will determine if proposed health care or care already delivered is the correct intervention and level of quality. It also allows a user to monitor the appropriateness of the amount of resources expended. Based upon the user, some of the decisions will cause cases to be referred to a higher level of authority, for example from a nurse to a physician, rather than allowing the ultimate decision to be made at the lower level. A decision maker at the highest level of review will have the flexibility of accessing the same tools utilized at all other user levels and be able to review an historical generation of information on the particular case or patient.

The tools provided by the present invention present criteria that help a decision maker screen a case for appropriateness or inappropriateness, decide if further review is needed by a higher level of authority, state policy, negotiate a compromise, and/or make an ultimate decision. The four different models provided are referred to as the "informational", "synopsis", "structured", and "guided" models. The informational model provides reference material, clinical guidelines and/or clinical policy presented in a manner that supports independent decision making. It is used to provide up-to-date support to a user, such as a nurse or physician, to assist the user in learning about and making an informed decision as to the problem at hand. The synopsis model is similar to the informational model, but only provides a limited amount of information. For example, in the health care field, the synopsis model may contain disease or condition specific information to provide a general overview on a relevant topic.

The structured and guided models are used to obtain information relating to the problem at hand required by an expert system component of the decision making system. The structured model provides formatted questions with branching logic tables and/or an array that will lead the user to a set decision based on the answers to the questions presented. The guided model provides open-ended questions which elicit information (such as clinical information) and provide the guideline criteria for each question to guide a user in making decisions. The guided model is used by experienced users, whereas the structured model is used by lower level or inexperienced users.

The decision making system of the invention places decision making in the hands of the end user. At the lowest level, the system generates a finite recommendation to the user, through the use of the structured model. At the next level of review, the guided model is used to assist the user by generating a recommendation for a decision. The user has the ability to override the system generated recommendation in the guided model. At a higher level of decision making, the system allows for review of information considered during the lower levels, to enable a high level reviewer (e.g., a physician) to make an independent informed decision. Free navigation from one topic area to another is provided among the models. Further, easy access is provided to an extensive library of relevant information useful in making a decision via the informational and synopsis models. Each of the models is implemented via software in a user workstation, such as a desktop personal computer coupled to one or more central databases via a local area or wide area network or the like.

In accordance with a first embodiment of the present invention, a computer system is provided for use in managing the health care of individual patients. A user interface is provided for entering a description of a medical condition and a proposed treatment therefor. Database means store a topical library of medical information. Means are provided for searching the topical library to identify medical information relevant to the medical condition and proposed treatment descriptions entered via the user interface. Means are provided for enabling a user to access, via the user interface, medical information identified by the searching means to assist the user in assessing the appropriateness of the proposed treatment. Expert system means provide interactive assistance to the user as to the appropriateness of the proposed treatment based on information entered via the user interface and rules associated with the expert system means.

The computer system has particular applicability to evaluating medical insurance claims. In such an embodiment, the expert system means include means for making recommendations as to whether or not the proposed treatment should be approved for insurance coverage. The expert system means can include means for suggesting alternatives to the proposed treatment. The expert system means can further include means for providing the user with an explanation of the logic it used to make a recommendation and/or to suggest an alternative.

The expert system means can include means for analyzing a plurality of different medical conditions entered by a user. In such an embodiment, the expert system means factors each of the medical conditions into its recommendation as to whether or not the proposed treatment should be approved for insurance coverage.

The system also provides a user interaction file that maintains a record of: (1) the medical condition and proposed treatment entered by the user, (2) the medical information identified by the searching means and accessed by the user, and (3) the recommendation made by the expert system means. Means are provided for retrieving the user interaction file during a subsequent session involving the health care management of a patient to which the user interaction file relates. The expert system considers information in the retrieved user interaction file before making a recommendation as to a new proposed treatment for the patient. The system can further comprise means for storing insurance policy information for use in assisting a user to determine whether the proposed treatment is covered by a patient's insurance policy.

The expert system means can be implemented to facilitate the input of the medical condition and proposed treatment descriptions together with relevant patient information in either a guided or structured mode. The structured mode is directed to inexperienced users and dynamically generates questions in response to previous answers provided by the user, to enable the expert system means to make a recommendation as to the appropriateness of the proposed treatment. The guided mode is directed to experienced users and provides an open-ended questionnaire enabling the user to decide which questions to answer to obtain a recommendation as to the appropriateness of the proposed treatment. A user interaction file can be provided that maintains a record of a guided or structured dialog with the user including the medical condition and proposed treatment entered by the user, the medical information identified by the searching means and accessed by the user, and the recommendation made by the expert system means.

The searching means can include means for providing context-sensitive assistance to the user by generating a key word search through the topical library in response to information entered by the user. The topical library preferably contains synopses of the medical information, in which case the system further includes means for enabling a user to access either a synopsis or a full record of medical information identified by the searching means.

An expert system is provided in accordance with the invention for interactively assisting a user in solving other types of problems, which are not necessarily medically related. The expert system includes a user interface for entering a description of a problem and a proposed solution therefor. Database means are provided for storing a topical library of information, including synopses and more complete information relevant to the problem and the proposed solution. Means are provided for searching the topical library to identify the synopses and information relevant to the problem and proposed solution. A user is enabled to selectively access, via the user interface, synopses and information identified by the searching means for assistance in assessing the appropriateness of the proposed solution.

An inference engine provides interactive assistance to the user as to the appropriateness of the proposed solution based on information entered via the user interface and rules associated with the inference engine. In a preferred embodiment, the inference engine provides a recommendation as to whether the proposed solution should be adopted. The expert system can further comprise means for suggesting alternatives to the proposed solution. Means may also be provided for setting forth an explanation of the logic used to make the recommendation and/or to arrive at the suggested alternatives. The expert system can further comprise means for facilitating the input of the problem and proposed solution together with additional information via the user interface in either a guided or structured mode, and to provide a user interaction file, as indicated above.

In another embodiment, an expert system is provided for interactively assisting a user in solving problems in a guided or structured mode. A description of a problem and proposed solution are entered via a user interface. Database means store a topical library of information, including information relevant to the problem and proposed solution. The topical library is searched to identify the information relevant to the problem and proposed solution. The user can access, via the user interface, information identified by the searching means to assist in assessing the appropriateness of the proposed solution. An inference engine provides a recommendation to the user as to the appropriateness of the proposed solution based on information entered via the user interface and rules associated with the inference engine. The inference engine comprises means for facilitating the input of the problem and proposed solution together with additional information via the user interface in either a structured or guided mode.

The structured mode is directed to an inexperienced user and dynamically generates questions in response to previous answers provided by the user, thereby enabling the inference engine to make a recommendation as to the appropriateness of the proposed solution. The guided mode is directed to experienced users and provides an open-ended questionnaire enabling the user to decide which questions to answer to obtain a recommendation as to the appropriateness of the proposed solution. A user interaction file is provided that maintains a record of a guided or structured dialog with the user including the problem and proposed solution entered by the user, the information identified by the searching means and accessed by the user, and the recommendation made by the inference engine.

DETAILED DESCRIPTION OF THE PREFERRED EMBODIMENTS

The present invention provides an "expert" computer system for use in assessing proposed solutions to problems. The invention is particularly well suited to the comprehensive management of the health care of individual patients. It is also useful in virtually any other field of endeavor, including the management of industrial processes, design engineering, research and development, education, and any other task in which a problem needs to be solved and one or more available solutions needs to be assessed in order to solve the problem.

A particular advantage of the system disclosed herein is that different user levels are accommodated. For example, a beginning user will need more structure in order to effectively interact with the expert system. In such a case, the system generates a questionnaire "on the fly," as the user is responding to previously asked questions. If the user asks for a recommendation from the expert system before all of the necessary information has been determined, the system will generate additional questions until all necessary information has been obtained. For more advanced users, a guided mode of operation is provided in which a predefined form is dynamically created based on an initial problem statement (e.g., medical diagnosis and proposed treatment) entered by the user. Information provided in the problem statement is used to index various questions or question categories maintained in a database. The appropriate questions are then retrieved and assembled into a questionnaire for display to the user. The advanced user then completes those areas of the questionnaire that he or she knows are necessary to obtain a recommendation from the system as to the validity of a proposed solution. In applications where the system is used for managing health care, a "problem" to be solved can comprise a medical condition or diagnosis for which it is necessary to find a treatment, and the solution to be assessed can comprise a proposed treatment for the medical condition.

The system also provides users with a vast array of information which is useful and/or necessary in order to understand the problem presented and the proposed solution. Again, in the health care management application, such information can comprise medical journal publications, medical terminology definitions, clinical guidelines, and acceptable treatments for the condition under consideration. In accordance with the present invention, such information can be presented to the user in either an abridged ("synopsis") or unabridged ("information") form.

Figure 1:
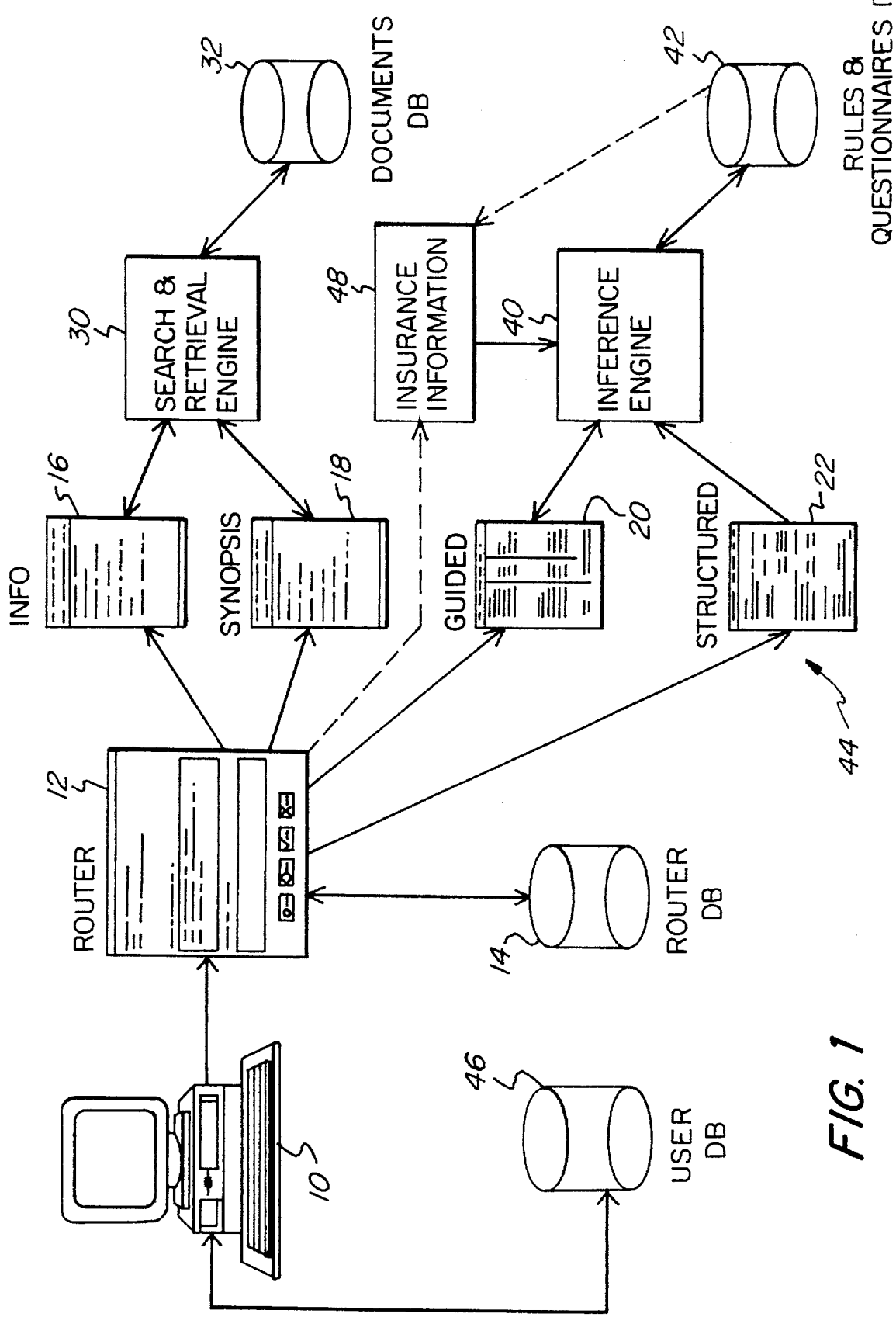
FIG. 1 is a block diagram of an expert system in accordance with the present invention.

A general block diagram of the system is provided in FIG. 1. A user interfaces with the system via a user interface 10, which can comprise a desktop personal computer ("PC"). The user interface is connected through a wide area network, local area network or other communication path to various databases 14, 32 and 42 explained in greater detail below. A router software module 12 runs on the user interface PC and enables the user to interact with the problem solving system software modules generally designated 44. These modules can also run locally on the user interface PC.

Preferably, the user interface 10 includes a graphical user interface such as the Microsoft Windows operating environment. The functions of router module 12 are selectable via one or more windows provided on the user display. A router database 14 provides the router screen displays and other data necessary to enable a user to interact with the system via the user interface 10.

Router 12 will initially prompt a user for demographic data defining the problem, a proposed solution, and other background information which in the case of a health care management system can comprise a patient's name, age, sex, insurance identification and other identifying data. Where the case currently under consideration was previously assessed by the system, a user interaction file from the previous session is retrieved, e.g., from a user database 46 at the user location, and passed on to the problem solving system 44 via the router so that the problem solving system will have a history of prior transactions concerning the case currently under consideration.

Once the user has entered the basic information into the system, including the problem to be solved and the proposed solution to be assessed, router 12 will pass this information to an information subsystem 16 and a synopsis subsystem 18. These subsystems provide two means for a user to access technical information about the problem and proposed solution. In the information mode, the user will be able to view detailed documentation concerning the problem and/or proposed solution. In the medical context, this information can include medical journal articles, medical definitions, insurance company guidelines, and the full text of other relevant information. In the synopsis mode, a summary of the technical information is available for viewing by the user.

The information and synopses that can be presented by the information and synopsis subsystems is located by a search and retrieval engine 30 from a documents database 32. The search and retrieval engine 30 can comprise, for example, a commercial product such as the Verity Topic™ database retrieval system available from Verity, Inc. of Mountainview, Calif., U.S.A. The search and retrieval can be implemented using key word searching, so that current information is always retrieved from database 32 which is updated on a regular basis. Thus, as new information (e.g., medical journal articles) becomes available, it is entered into database 32 and will be available to a user via the information and synopsis subsystems 16, 18, respectively. This approach is preferable to a hard coded "hypertext" approach, in which each problem and proposed solution description that can be entered by a user is hard coded to the information relevant thereto in database 32. Such a hard coded approach would require a new cross reference table to be created every time new information is added to database 32. Such a tedious and time consuming process is avoided by utilizing key word searching via search and retrieval engine 30.

In order to further facilitate the efficient operation of the system in the medical context, the medical condition and proposed treatment can be entered by the user by simply inputting standardized diagnosis and treatment codes (e.g., "ICD-9" codes) already in use by the medical community. Such codes are numeric or alphanumeric sequences that will be familiar to anyone who has ever received an insurance submission form from a physician. Each numerical code designates a different diagnosis or procedure, and provides an easy way to enter the medical condition and proposed treatment into the system of the present invention.

After search and retrieval engine 30 obtains a description of each of the relevant information articles and synopses available in database 32, these descriptions are presented to the user in the form of a topical list presented on the display of user interface 10. The display will also present the user with an opportunity to enter into a guided mode or structured mode of interaction with the expert system.

The expert system intelligence is provided by an inference engine 40. If a user enters the expert system in a guided mode 20, he will be presented with a dynamically generated questionnaire accessed from rules and questionnaire database 42 by inference engine 40. The questions for guided mode questionnaires are developed in advance using an appropriate authoring tool, and loaded into database 42 for future retrieval and assembly by the inference engine 40 into a questionnaire that is relevant to the specific problem and proposed solution entered. Thus, the guided mode questionnaire will contain a series of open-ended questions and key elements relevant to the particular problem (e.g., medical condition) and proposed solution (e.g., treatment) under consideration.

The guided mode is used by an experienced user, who will know which questions on the questionnaire must be answered and which merely provide additional information to assist the inference engine in making a recommendation as to the proposed treatment. The questions presented in the guided mode are designed to elicit and evaluate clinical information, support the capture of data from the user, and enable a decision to be recommended. The user is in control of which questions to answer and the order in which the answers are provided. The user may accept the system recommendation (i.e., whether or not to approve or "certify" the proposed treatment) or elect to override it.

A less experienced user can interact with the inference engine 40 in the structured mode 22. In this mode, specific questions are presented to the user by the system. The questions guide the user through the decision making process in a very structured way, and are generated dynamically by the inference engine 40 on the basis of the user's responses to previous questions. It should be appreciated that in the structured mode, the questions are presented, e.g., one at a time, in response to the user's previous answers, whereas in the guided mode, a complete questionnaire is initially generated and presented to the user on the basis of the initial problem and proposed treatment information input by the user. The operation of the inference engine 40 is guided at all times by rules stored in database 42.

In addition to providing a recommendation as to whether or not to accept a proposed solution to a problem, inference engine 40 can also be provided with rules to enable it to suggest alternative solutions (e.g., medical treatments or care options). In medical applications, the expert system can also access information concerning insurance policy coverage ("insurance information" 48) from database 42 or via router 12 from database 14, to make a determination as to whether a proposed treatment is covered by a particular patient's medical insurance policy.

The inference engine can also provide an explanation of the logic it used to make a particular recommendation and/or to suggest alternatives to a proposed solution. This is particularly helpful in the event that a recommendation was made by the system or the user to refer the case to a more experienced reviewer, such as a physician, to make a final decision as to whether the proposed treatment should be certified or not. By having an explanation as to why the case was referred, the reviewer will be able to more quickly focus on the relevant issues that must be addressed to arrive at a final decision.

The information output from inference engine 40 is forwarded to router 12 at the user interface 10. Output from the inference engine can also be packaged by router 12 into a user interaction file that maintains a record of the problem and proposed solution entered by the user, together with the information identified by the searching means and accessed by the user. This user interaction file can be stored in router database 14 or in a separate user database 46 for subsequent use when dealing with the same case, for example, during a subsequent session involving the health care management of the patient to which the user interaction file relates.

Figure 2:
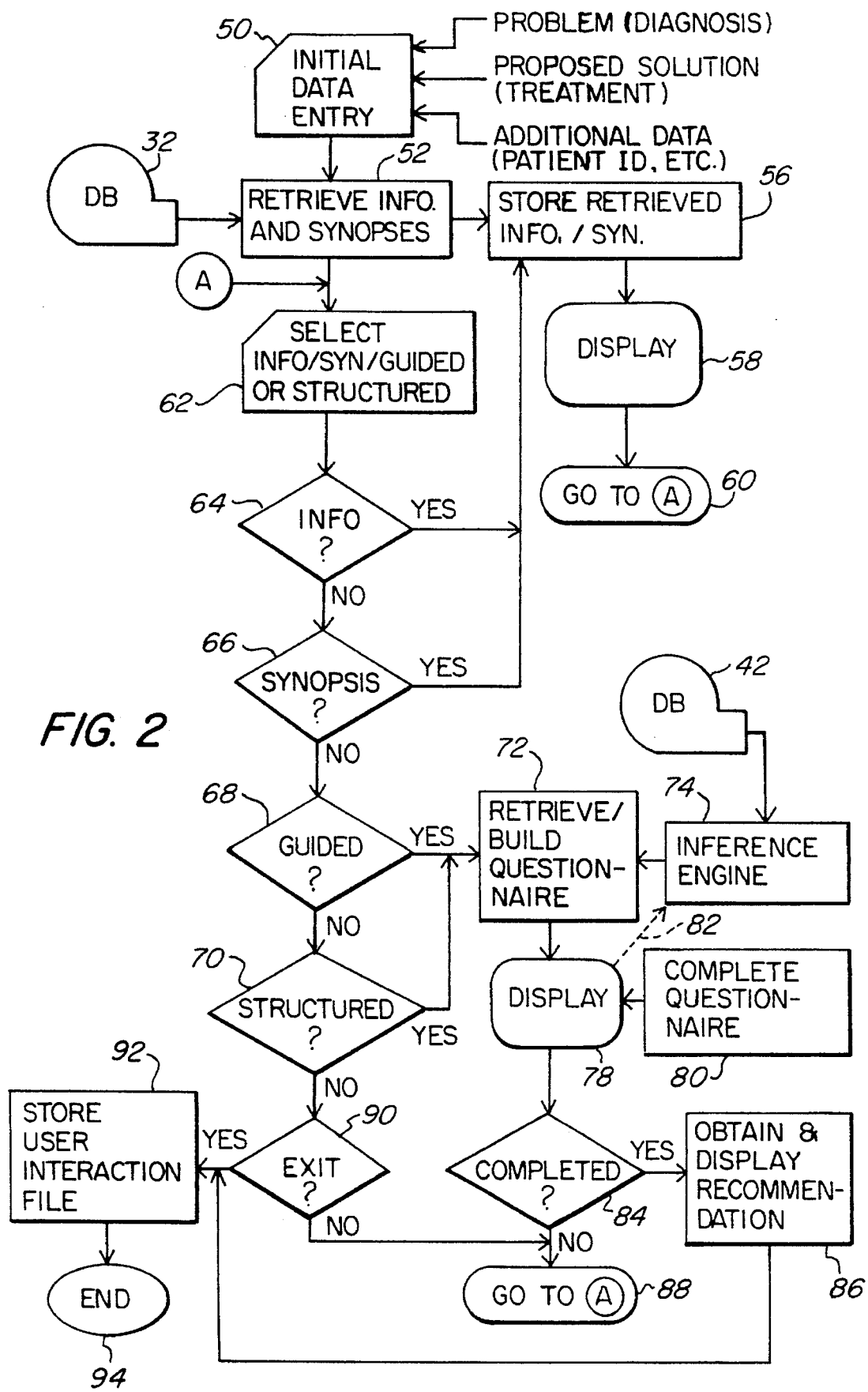
FIG. 2 is a flowchart illustrating the operation of the expert system.

The use and operation of the system of the present invention is further illustrated by the flowchart of FIG. 2. In the following discussion of FIG. 2, it is assumed that the system is being used in connection with the health care management of a patient. However, it should be understood that this is only an example of one of many applications that can be provided by the system. The following discussion is in no way intended to limit the scope of the invention as set forth in the claims.

The routine of FIG. 2 commences at box 50, which is where the user enters initial data via the user interface. Such data will include the patient's medical condition (i.e., diagnosis) as well as a proposed solution (i.e., treatment) for the medical condition. Additional data, such as the patient's identification, address, physician, etc. is also entered at this point.

The diagnosis and treatment information can be entered in the form of standard numeric or alphanumeric medical codes. The diagnosis can comprise a plurality of different medical conditions which must be factored into the ultimate decision as to whether the proposed treatment is proper. The proposed treatment can comprise medical procedures, a hospital release, long-term care, or the like. It should also be appreciated that the initial data entry by the user can be preceded by retrieval of a user interaction file for a previous session concerning the same patient.

After the initial data is entered, the system will retrieve relevant information and synopses from database 32 as indicated at box 52. The retrieved information and synopses are stored, either in their full text form or as a list of descriptors that can later access database 32 for the full records, as indicated at box 56.

After the information and synopses relevant to the problem and proposed solution have been retrieved and stored, the user is given an opportunity to select either information for viewing, one or more synopses for viewing, or to embark upon a guided or structured interaction with the inference engine. This step is indicated at box 62. In the event the user selects to view information as determined at box 64, the stored information is retrieved via box 56 and displayed on the user terminal as indicated at box 58. After the user is finished with the displayed information, it can be cleared or maintained in an open window for later viewing. The routine then returns to box 62 as indicated at box 60, where the user can again select either information, synopses, or a guided or structured session with the inference engine.

If the user elects to view a synopsis of information relevant to the problem and proposed solution, the synopsis will be displayed on the user's terminal as indicated by boxes 66, 56, and 58. Then, via box 60, the user is again able to select further information, a further synopsis, or a guided or structured interaction as indicated at box 62.

If the user selects a guided interaction with the inference engine, as determined at box 68, a predetermined questionnaire corresponding to the problem and proposed solution will be generated as indicated at box 72 from database 42 via the inference engine as indicated at box 74. The retrieved questionnaire is displayed on the user terminal as indicated at box 78, and the user inputs the information necessary to complete the questionnaire as indicated at box 80. For example, where the diagnosis is pediatric asthma, the guided questionnaire may ask for clinical findings such as accessory muscle use/retractions, auscultatory findings; $PCO_2$ level, dyspnea, mental status, $O_2$ saturation, $PO_2$ level, peak exploratory flow rate, pulsus paradoxus, respiration rate, skin color, etc. Additional factors may also be noted, such as history of previous respiratory failure, recurrent status asthmaticus, prior use of IV isoproterenol, prior use of controlled ventilation, use of systemic corticosteroids, EKG abnormalities, etc. The information entered by the user will all be factored into a recommendation by the inference engine as to a course of action.

In the guided mode, the user does not have to answer every question on the questionnaire. The user will be experienced enough to know which questions must be answered and which merely provide optional information that is useful to the inference engine. In a preferred embodiment, the questions that are required to be answered are marked as such on the questionnaire that is displayed to the user.

Once the user has completed the questionnaire, this fact is determined at box 84, and at box 86 a recommendation is obtained from the inference engine as to whether or not to approve the proposed treatment. The inference engine makes a recommendation based on rules contained in database 42 and the information contained in the completed questionnaire, as indicated by dashed arrow 82. After the recommendation has been obtained, it is displayed to the user and stored together with the complete user dialog to that point in a user interaction file, as indicated at box 92. The routine then ends at box 94.

In the event that the user selected a structured interaction with the inference engine at box 62, as determined at box 70, individual questions relevant to the problem and proposed solution are presented by the inference engine as indicated at box 72 based on rules contained in database 42. These questions may be a subset of those provided on the guided questionnaire for the same problem and proposed solution, as well as additional questions eliciting specific information that a more experienced user would simply volunteer in a guided mode interaction with the inference engine. The specific questions presented by the inference engine are displayed to the user (e.g., one or more at a time) as indicated at box 78, and the user completes the questions as indicated at box 80 in the order presented by the inference engine. The inference engine uses the answers to the questions, as indicated via dashed arrow 82, to generate additional questions for display to the user. In this manner, a complete questionnaire is dynamically built and answered to enable the inference engine to make a recommendation as to the acceptability of the proposed treatment.

When the questionnaire has been completed and all requested information answered, as determined at box 84, the recommendation of the inference engine is obtained and displayed to the user as indicated at box 86. A user interaction file is then created and stored as indicated at box 92, and the routine ends at box 94.

The user can exit the system without completing the recommendation process by selecting "exit" at box 62, which will be determined by box 90. At this point, the user interaction file as it exists to the point of exit will be stored as indicated at box 92, and the routine will end at box 94. In the event that a user fails to complete a questionnaire such that the inference engine does not have the information necessary to provide a recommendation, this fact will be determined at box 84 and the user will be returned to box 62 via box 88 where further information or synopses can be selected (e.g., to enable the user to answer a question presented in the questionnaire) or to exit the current session.

It should now be appreciated that the present invention provides an expert problem solving system that is operable on different levels (guided and structured) to obtain recommendations as to the acceptability of a proposed solution to a problem. The invention is particularly advantageous for use in the comprehensive management of health care, although it is by no means limited to such an application. Information is available to the user in either a full text or synopsis form, and can be accessed before or during interaction with the inference engine. The user interface is simple and straightforward, and is easily implemented in a windows operating environment. Maintenance of user interaction records enables comprehensive case management to be provided with a full understanding of the prior case history.

Although the invention has been described in connection with a specific embodiment thereof, those skilled in the art will appreciate that numerous adaptations and modifications may be made thereto without departing from the spirit and scope of the invention as set forth in the claims.

We claim:

1. A computer system for use in medical case management comprising:

a user interface selectively operable in a guided mode for experienced users and a structured mode for inexperienced users, said user interface enabling the input of information identifying a patient, a description of at least one medical condition of said patient and a proposed treatment for said medical condition;

a database for storing a topical library of medical information;

means for searching said topical library to identify medical information relevant to the medical condition and proposed treatment entered via said user interface;

means for enabling a user to access, via said user interface, medical information identified by said searching means to assist the user in assessing the appropriateness of said proposed treatment; and an expert system including a rules database for supplementing the assistance provided by said searching means, said expert system being accessible by said user interface for providing a recommendation as to the appropriateness of said proposed treatment based on information entered via said user interface and rules recovered from said rules database;

said expert system facilitating the input of information via said user interface in said structured mode by dynamically generating questions in response to previous answers provided by the user to enable the expert system to make said recommendation; and said expert system facilitating the input of information in said guided mode by providing a predefined questionnaire enabling the user to decide which questions to answer to obtain said recommendation.

2. A computer system in accordance with claim 1, wherein said expert system is responsive to the information entered via said user interface and rules recovered from said rules database for providing a recommendation as to whether said proposed treatment should be certified for coverage by an insurer.

3. A computer system in accordance with claim 2 wherein said expert system includes means for analyzing a plurality of different medical conditions entered via said user interface, said expert system factoring each of said medical conditions into a recommendation as to whether or not the proposed treatment should be certified for coverage by said insurer.

4. A computer system in accordance with claim 2 wherein said expert system includes means for providing said user with an explanation of the logic it used to make a recommendation.

5. A computer system in accordance with claim 1 wherein said expert system includes means for providing said user with an explanation of the logic it used to make a recommendation.

6. A computer system in accordance with claim 1 wherein said expert system includes means for suggesting alternatives to said proposed treatment.

7. A computer system in accordance with claim 1 further comprising:

means for providing a user interaction file that maintains a record of the medical condition and proposed treatment entered by said user, the medical information identified by said searching means and accessed by said user, and the recommendation made by said expert system means.

8. A computer system in accordance with claim 7 further comprising:

means for retrieving said user interaction file during a subsequent session involving the case management of a patient to which said user interaction file relates;

wherein said expert system considers information in the retrieved user interaction file before making a recommendation as to a new proposed treatment for said patient.

9. A computer system in accordance with claim 1 further comprising:

means for providing a user interaction file that includes a record of a guided or structured dialog with said user, including the medical condition and proposed treatment entered by said user, the medical information identified by said searching means and accessed by said user, and the recommendation made by said expert system means.

10. A computer system in accordance with claim 9 further comprising:

means for retrieving said user interaction file during a subsequent session involving the case management of a patient to which said user interaction file relates;

wherein said expert system considers information in the retrieved user interaction file before making a recommendation as to a new proposed treatment for said patient.

11. A computer system in accordance with claim 1 wherein said searching means include means for providing context sensitive assistance to said user by generating a key word search through said topical library in response to information entered by the user.

12. A computer system in accordance with claim 11 wherein said topical library contains synopses of said medical information, said system further including means for enabling a user to access either a synopsis or a full record of medical information identified by said searching means.

13. A computer system for use in medical case management comprising:

a user interface for enabling the input of information identifying a patient, a description of at least one medical condition of said patient and a proposed treatment for said medical condition;

a database for storing a topical library of medical information;

means for searching said topical library to identify medical information relevant to the medical condition and proposed treatment entered via said user interface;

means for enabling a user to access, via said user interface, medical information identified by said searching means to assist the user in assessing the appropriateness of said proposed treatment; and an expert system including a rules database and being accessible by said user interface for providing recommendations as to the appropriateness of said proposed treatment and as to whether said proposed treatment should be certified for coverage by an insurer, based on information entered via said user interface and rules recovered from said rules database.

14. A computer system in accordance with claim 13 wherein said expert system includes means for analyzing a plurality of different medical conditions entered via said user interface, said expert system factoring each of said medical conditions into a recommendation as to whether or not the proposed treatment should be certified for coverage by said insurer.

15. A computer system in accordance with claim 14 wherein said expert system includes means for providing said user with an explanation of the logic it used to make a recommendation.

16. A computer system in accordance with claim 13 wherein said expert system includes means for providing said user with an explanation of the logic it used to make a recommendation.

17. A computer system in accordance with claim 13 wherein said expert system includes means for suggesting alternatives to said proposed treatment.

18. A computer system in accordance with claim 13 further comprising:

means for providing a user interaction file that maintains a record of the medical condition and proposed treatment entered by said user, the medical information identified by said searching means and accessed by said user, and the recommendation made by said expert system means.

19. A computer system in accordance with claim 18 further comprising:

means for retrieving said user interaction file during a subsequent session involving the case management of a patient to which said user interaction file relates;

wherein said expert system considers information in the retrieved user interaction file before making another recommendation.

20. A computer system in accordance with claim 13 wherein said searching means include means for providing context sensitive assistance to said user by generating a key word search through said topical library in response to information entered by the user.

21. A computer system in accordance with claim 20 wherein said topical library contains synopses of said medical information, said system further including means for enabling a user to access either a synopsis or a full record of medical information identified by said searching means.

\* \* \* \* \*